United States Patent
Li et al.

(10) Patent No.: US 7,803,398 B2
(45) Date of Patent: Sep. 28, 2010

(54) TARGETED DELIVERY SYSTEM

(75) Inventors: Shyh-Dar Li, Toufen Township, Miaoli County (TW); Ae-June Wang, Hsinchu (TW); Leaf Huang, Hsinchu (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 1434 days.

(21) Appl. No.: 11/020,773

(22) Filed: Dec. 23, 2004

(65) Prior Publication Data

US 2005/0142181 A1    Jun. 30, 2005

(30) Foreign Application Priority Data

Dec. 31, 2003    (TW) .............. 92137621 A

(51) Int. Cl.
*A61K 9/127*    (2006.01)
(52) U.S. Cl. .................... 424/450; 424/489
(58) Field of Classification Search ............ 424/450
See application file for complete search history.

(56) References Cited

U.S. PATENT DOCUMENTS

| | | | |
|---|---|---|---|
| 5,298,509 A | 3/1994 | Schuster et al. | 514/284 |
| 5,552,404 A | 9/1996 | Chang et al. | 514/255 |
| 5,574,159 A | 11/1996 | Chang et al. | 544/396 |
| 5,658,908 A | 8/1997 | Chang et al. | 514/252 |
| 5,679,673 A | 10/1997 | Bowen et al. | 514/221 |
| 5,679,679 A | 10/1997 | Bowen et al. | 514/249 |
| 5,681,830 A | 10/1997 | Chang et al. | 514/85 |
| 5,739,158 A | 4/1998 | de Costa et al. | 514/429 |
| 5,854,249 A | 12/1998 | Chang et al. | 514/255 |
| 5,856,318 A | 1/1999 | Bowen et al. | 514/183 |
| 5,911,970 A | 6/1999 | John et al. | 424/1.85 |
| 5,919,797 A | 7/1999 | Goodman et al. | 514/319 |
| 5,958,920 A | 9/1999 | Bowen et al. | 514/214 |
| 5,993,777 A | 11/1999 | John et al. | 424/1.81 |
| 6,015,543 A | 1/2000 | John et al. | 424/1.81 |
| 6,316,024 B1 * | 11/2001 | Allen et al. | 424/450 |
| 6,447,748 B1 | 9/2002 | John et al. | 424/1.85 |
| 6,517,811 B2 | 2/2003 | John et al. | 424/1.81 |
| 6,573,101 B1 * | 6/2003 | Goomer | 435/458 |
| 6,602,877 B1 | 8/2003 | Bamborough et al. | 514/256 |
| 6,749,863 B1 * | 6/2004 | Chang et al. | 424/450 |
| 2004/0219205 A1 * | 11/2004 | Kan et al. | 424/450 |

FOREIGN PATENT DOCUMENTS

WO    01/98321    * 12/2001

OTHER PUBLICATIONS

"Targeting sigma receptor-binding benzamides as in vivo diagnostic and therapeutic agents for human prostate tumors" John et al.; 1999.
"Long-Circulating Emulsions (Oil-in-Water) as Carriers for Lipophilic Drugs" Feng Liu et al.; Pharmaceutical Research, vol. 12, No. 7, 1995 (Received Dec. 21, 1994; accepted Feb. 22, 1995).
"A Submicron Lipid Emulsion Coated with Amphipathic Polyethylene Glycol for Parenteral Administration of Paclitaxel (Taxol)" Bo B. Lundberg; J. Pharm Pharmacol. 1997, 49:16-21; Received Mar. 21, 1996, Accepted Apr. 19, 1996.

* cited by examiner

*Primary Examiner*—Gollamudi S Kishore
(74) *Attorney, Agent, or Firm*—Thomas, Kayden, Horstemeyer & Risley

(57) ABSTRACT

A targeting delivery system. The targeted delivery system includes a carrier for a drug and a targeted ligand modifying the carrier to target the encapsulated drug to a sigma receptor over-expressed cell.

13 Claims, 12 Drawing Sheets

TARGETED DELIVERY SYSTEM

BACKGROUND

The invention relates to targeted delivery technology. More particularly, the invention relates to a delivery system targeting sigma receptors over-expressed cells.

Anti-cancer drugs presently in clinical use have low therapeutic windows, resulting in serious side effects. Therefore, a targeted delivery system for delivering those toxic drugs to target cells is needed.

Nanoparticle delivery systems, such as liposomes, polymer-based delivery systems, or emulsions, are unable to target to specific cells. Therefore, targeted ligands that can modify the nanoparticle delivery systems are required for developing targeted delivery systems. However, antibodies, the most common used ligands in targeted drug delivery may cause serious immune response after systemic injection and this would be a potential problem.

Small molecule ligands with no immunogeneicity and ease for scale up production are more desirable for modifying delivery systems, thus are more potential for targeted delivery systems development compared to antibodies.

SUMMARY

Accordingly, an embodiment of the invention provides a targeted delivery system comprising a carrier for a drug; and a targeted ligand modifying the carrier to target the encapsulated drug to a sigma receptor (SR) over-expressed cell.

Also provided is a target delivery system comprising a drug and a targeted ligand conjugated therewith to targeted deliver the drug to a sigma receptor over-expressed cell.

BRIEF DESCRIPTION OF THE DRAWINGS

The invention can be more fully understood and further advantages become apparent when reference is made to the following description of the invention and the accompanying drawings in which:

FIG. 2A, 22B cells treated with LPDII; FIG. 2B, HONE-1 cells treated with LPDII; FIG. 2C, 22B cells treated with LPDII-AA; and FIG. 2D, HONE-1 cells treated with LPDII-AA. FIG. 2A~2D: 200×

DETAILED DESCRIPTION

Figure 1:
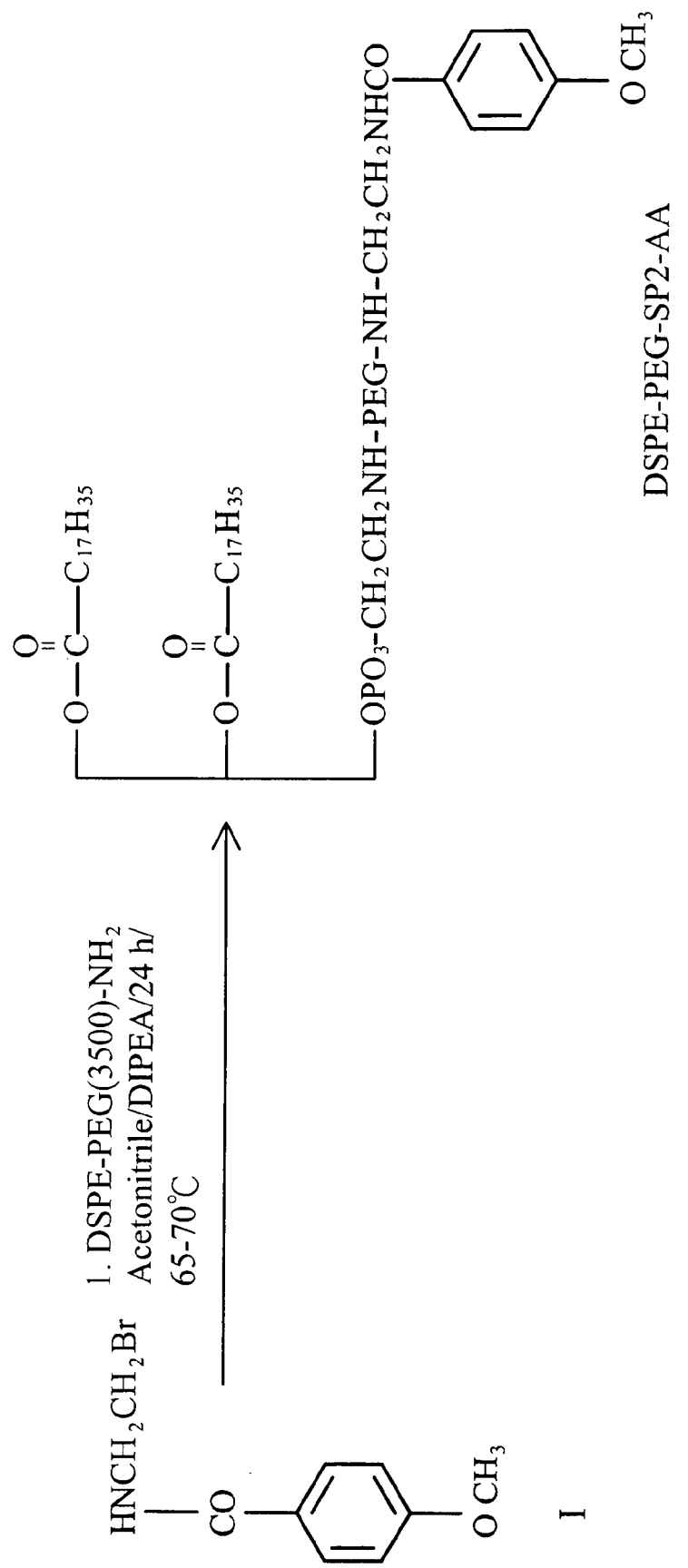
FIG. 1 illustrates the synthesis of ligand and its conjugation with lipid.
Figure 2A:
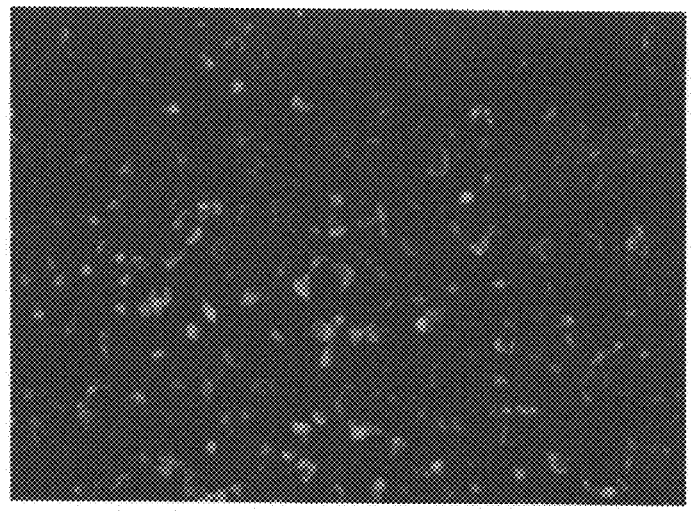
FIG. 2A-2D show the cellular uptake study results for head and neck cancer cells treated with FITC-oligonucleotide containing LPDII or LPDII-AA by fluorescence microscope.
Figure 2B:
Figure 2C:
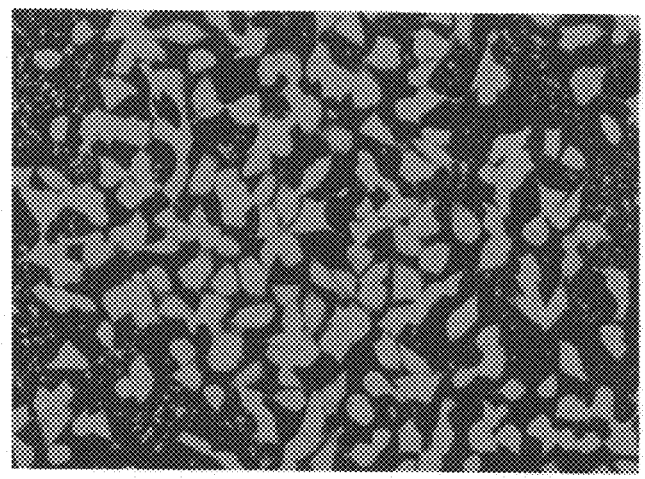
Figure 2D:
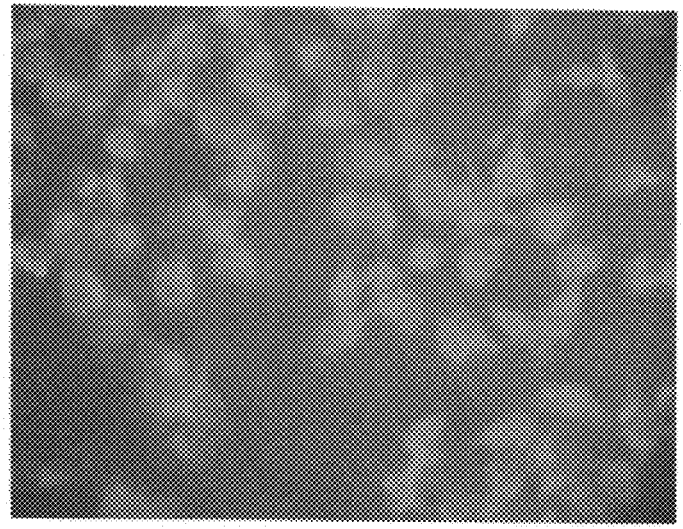

A variety of human tumors over-express SR, membrane-bound proteins that possess high affinity for haloperidol, various neuroleptics, and benzamide derivatives. Recently, researchers have synthesized a variety of benzamide derivatives and applied those new compounds for the treatment of cancers or as imaging agents for tissues which over-express SR.

The invention is based on the discovery of a targeted ligand, a benzamide derivative, anisamide (AA), originally used as an imaging agent in research for prostate cancer which over-express SR. We have conjugated AA ligands onto antisense oligonucleotide (AS-ODN) containing carriers and showed that these targeted carriers could specifically deliver AS-ODN into SR over-expressed cells.

The targeted delivery system of an embodiment of the invention, first of all, is an active targeting delivery system utilizing a molecule such as a ligand to recognize a specific receptor on the surface of a target cell for selective delivery of the drug into the target cell. When the ligands recognize the cell surface receptors, mechanism of receptor-mediated endocytosis is triggered and drugs containing carriers are uptaken by cells. SR is a cell surface receptor that can trigger endocytosis after binding with SR ligands.

Second, Benzamide derivatives, first proposed as small molecule compounds possessing high affinity for SR, have to date only been applied in tumor imaging, but firstly applied here as a targeted ligand for targeted delivery of drugs.

The targeting delivery system comprises a carrier for a drug and a sigma ligand modifying the carrier to target the encapsulated drug to a sigma receptor over-expressed cell.

Another target delivery system comprises a drug and a sigma ligand conjugated therewith to target delivery to a sigma receptor over-expressed cell.

The "targeted ligand" used herein comprises benzamide derivatives, preferably anisamide. Anisamide links to a lipid by chemical synthesis to form, for example, DSPE-PEG-SP2-AA (distearoylglycerolphosphatidylethanolamine-polyethyleneglycol(3400)-ω-[2-(4'-methoxybenzamido)] ethylamine). The modification of the carriers can thus be achieved.

The "carrier" used herein comprises nanoparticles. The nanoparticle comprises, but is not limited to, a liposome, a polymer based nanoparticle, or an emulsion; preferably a liposome.

The "drug" used herein comprises an organic compound, a peptide, a protein, an oligonucleotide, or DNA. When the carrier is a liposome, the drug can be an oligonucleotide, preferably an antisense oligonucleotide.

The "sigma receptor over-expressed cell" comprises a tumor cell. The tumor cell can be, but is not limited to, breast cancer, head and neck cancer, lung cancer, liver cancer, brain cancer, or prostate cancer. When the tumor cell is a head and neck cancer cell, the drug can be an antisense oligonucleotide of epidermal growth factor receptor (EGFR).

Practical examples are described herein.

EXAMPLES

Example 1

Synthesis of Ligand Conjugated Lipids

Compound of formula I was synthesized as shown in FIG. 1 in accordance with the method of M. T. Leffler and R. Adams. J Am Chem Soc. 59: 2252-2258 (1937). Compound of formula I was then reacted with DSPE-PEG-NH$_2$ dissolved in acetonitrile under diisopropylethyl amine (DIPEA) as a catalyst at 65~70° C. for 8 hours. DSPE-PEG-SP2-AA (distearoylglycerolphosphatidylethanolamine-polyethyleneglycol (3400)-ω-[2-(4'-methoxybenzamido)]ethylamine) was obtained.

Example 2

Preparation of Liposome-Protamine-DNA Complex, Type II (LPDII)

Control liposomes and AA-liposomes were prepared by thin film hydration. The former comprised N-glutaryl-dioleoyl phosphatidylethanolamine (N-glutaryl-DOPE), DOPE, and distearoyl-sn-glycerol-phosphatidylethanolamine-[ω-methoxypolyethylene glycol(3400)](DSPE-PEG-OCH$_3$) with a molar ratio of 49:49:2. The latter comprised N-glutaryl-DOPE, DOPE, and DSPE-PEG-SP2-AA with a molar ratio of 49:49:2. 0.1 mg/ml of the mixture of antisense oligonucleotide (AS-ODN) and calf thymus DNA, 1.1 mg/ml of protamine, and 0.3 mg/ml of liposome suspension were mixed in equal volume to form liposome-protamine-DNA complex, type II (LPDII). The mixture remained at room temperature for 10 minutes before use. The particle of LPDII was 150~200 nm in diameter and the encapsulation efficiency of oligonucleotide (ODN) was 100%. Unmodified LPDII represents as LPDII, and LPDII modified with anisamide ligands represents as LPDII-AA.

Example 3

Delivery of Oligonucleotide into Head and Neck Cancer Cells

Head and neck cancer cells, 22B and HONE-1, were seeded in 24-well plates one day before the experiment. Each well contained 5×10$^4$ cells. The cells were incubated with LPDII or LPDII-AA containing FITC-oligonucleotide in different concentrations at 37° C. for 4 hours and then washed with PBS three times. After that, the cells were fixed with 4% paraformaldehyde at 4° C. for 15 minutes and washed with PBS several times. The cells were observed under fluorescence microscope. The cells were, alternatively incubated with 1% triton X-100 in PBS at 37° C. for 1 hour. The cell lysates were then analyzed by fluorescence detector (λex: 494 nm, λem: 519 nm). The results were shown as fluorescence intensity of lysate.

Figure 3A:
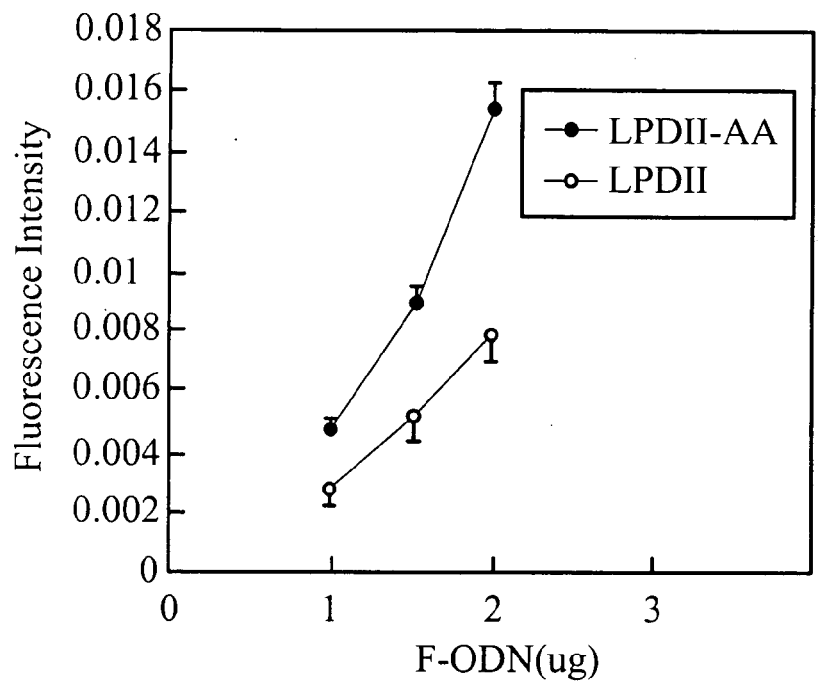
FIG. 3A~3B illustrate the delivery efficiencies of formula LPDII and LPDII-AA to head and neck cancer cells HONE-1 (FIG. 3A) and 22B (FIG. 3B).
Figure 3B:
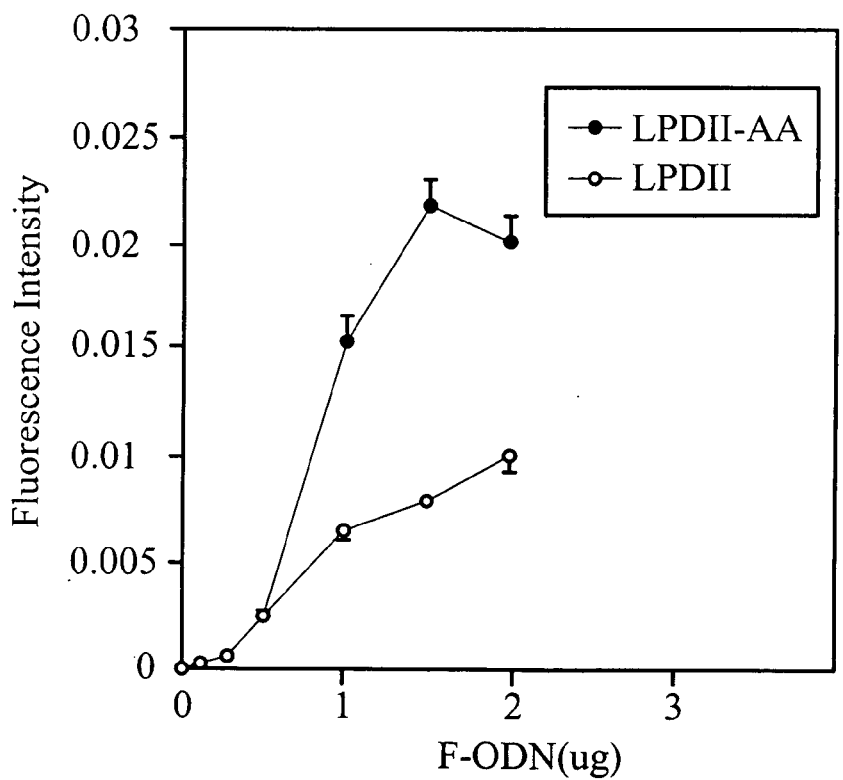
Figure 4:
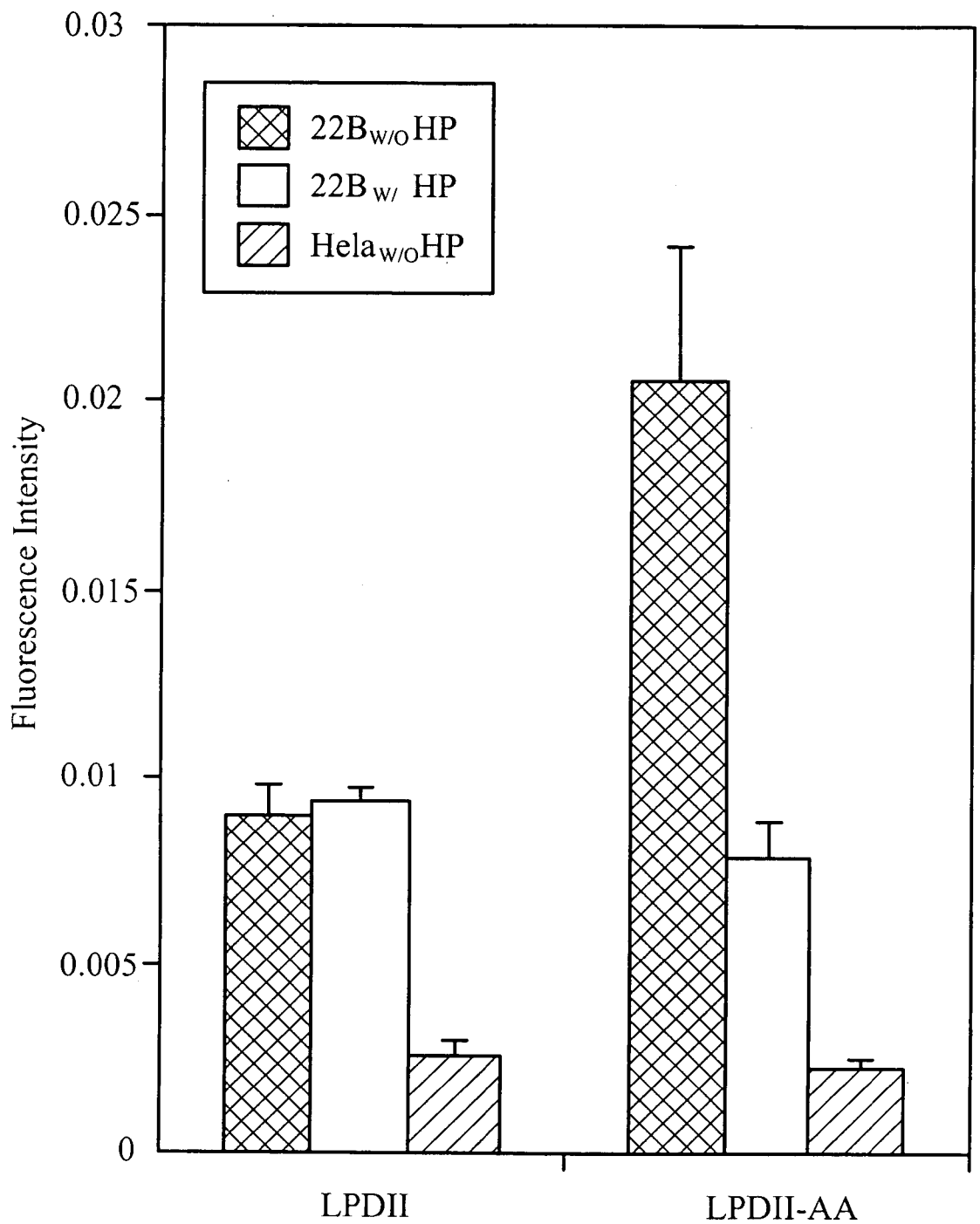
FIG. 4 illustrates the delivery efficiencies of formula LPDII and LPDII-AA to head and neck cancer cell, 22B, or cervical cancer cell, Hela, in the respective presence and absence of HP (haloperidol).

As shown in FIG. 2, LPDII-AA treated cells exhibited stronger fluorescence intensity than the cells treated with LPDII. This indicates that LPDII-AA delivers more ODN into head and neck cells. In quantitative study, as shown in FIG. 3, the delivery efficiency of LPDII-AA was 2~3 folds higer than that of LPDII. In competitive inhibition study, as shown in FIG. 4, the delivery efficiency of LPDII-AA was inhibited to the same level of LPDII in the presence of haloperidol (HP). For cervical cancer cell, HeLa, which do not express sigma receptors, the delivery efficiencies of LPDII-AA and LPDII showed no significant difference. These results indicate that AA ligand modified carriers (LPDII-AA) could specifically target to sigma receptor-over-expressed cells.

Example 4

In Vitro Efficacy Test 22B or HONE-1 cells were seeded in 24-well plates one day prior to the experiment conducted. The cells were incubated with free AS-ODN (against epidermal growth factor receptor)or AS-ODN containing LPDII or LPDII-AA at 37° C. for 4 hours. After that, medium was replaced and cells were incubated for another 72 hr. The vital cells were counted by trypan blue exclusion method thereafter.

The EGFR down-regulation study was conducted by quantitatively determining EGFR contents in cells with ELISA kits.

Figure 5A:
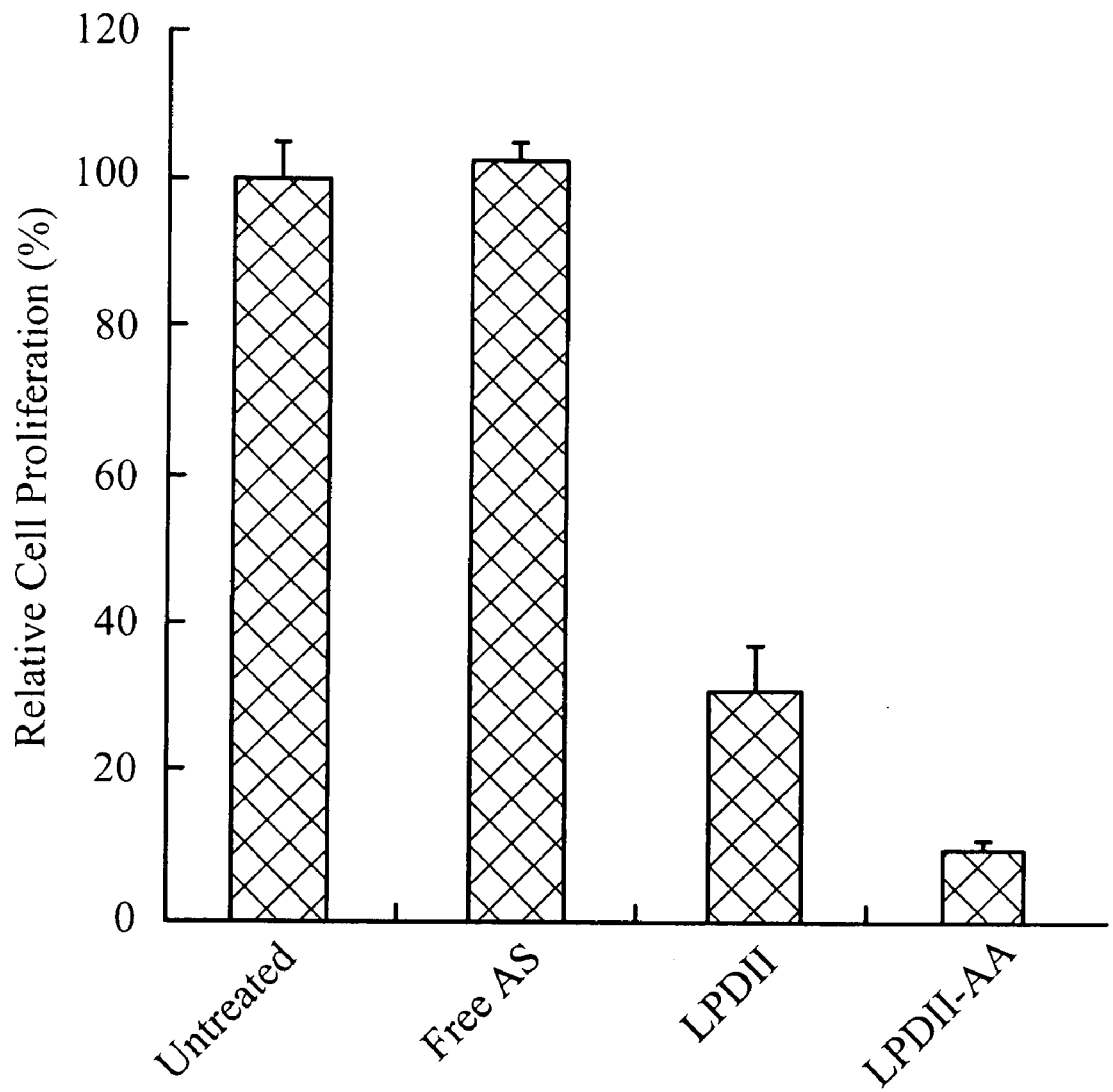
FIG. 5A~5B show cell proliferation inhibition of head and neck cancer cell, HONE-1 (FIG. 5A) and 22B (FIG. 5B), respectively untreated and treated with free AS, LPDII or LPDII-AA.
Figure 5B:
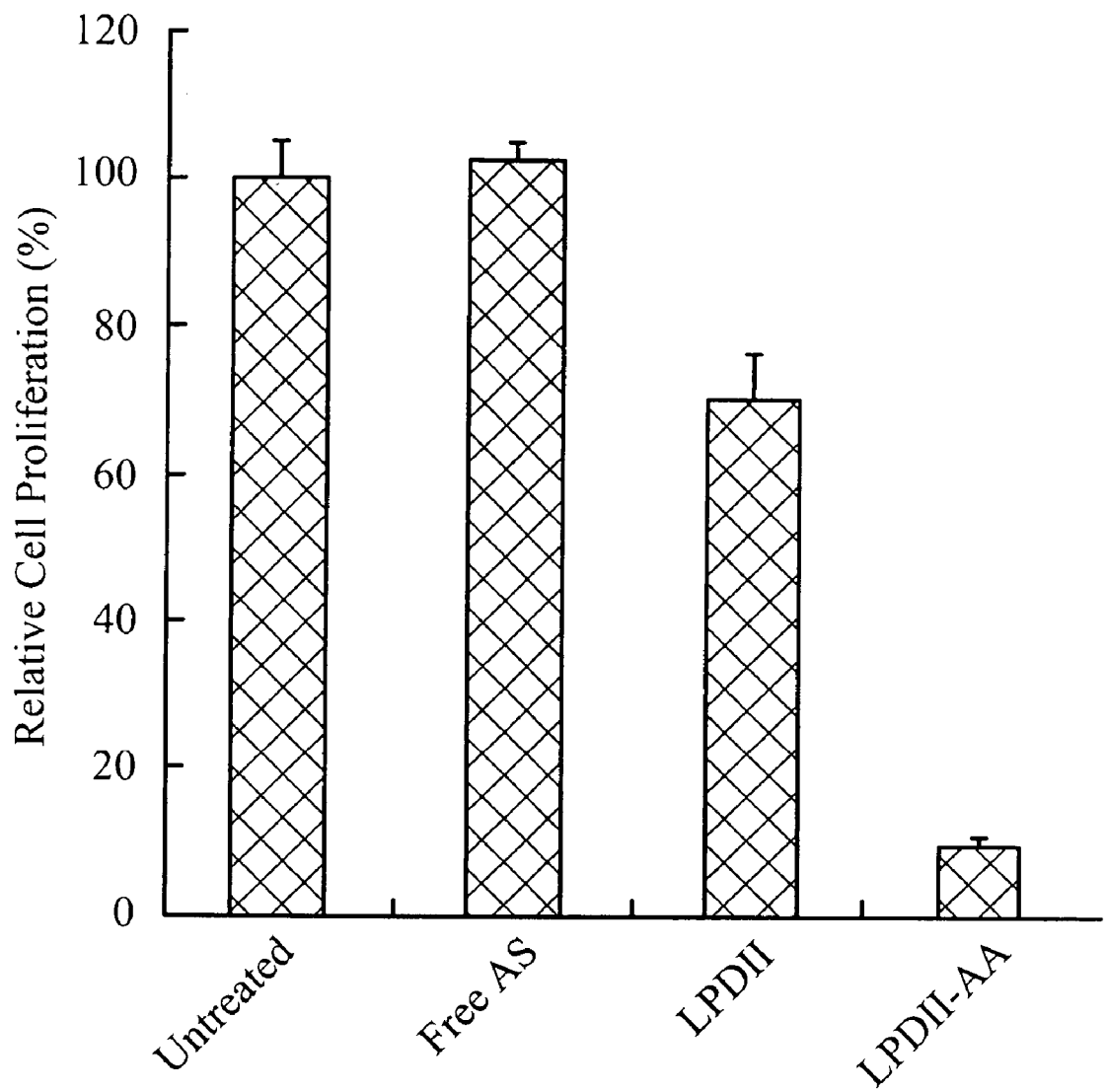
Figure 6A:
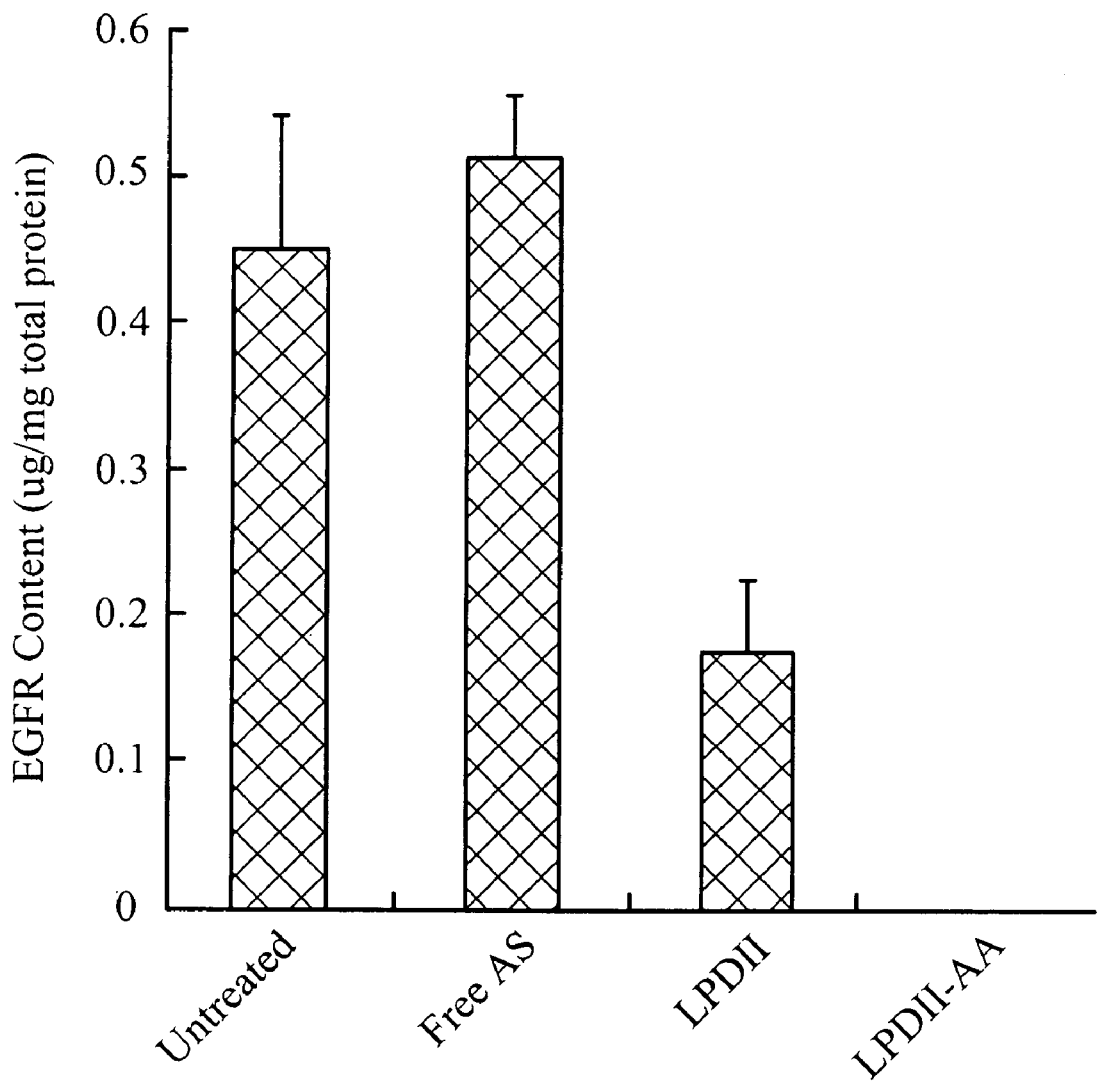
FIG. 6A~6B show EGFR down-regulation of head and neck cancer cell, HONE-1 (FIG. 6A) and 22B (FIG. 6B), respectively untreated and treated with free AS, LPDII, or LPDII-AA.
Figure 6B:
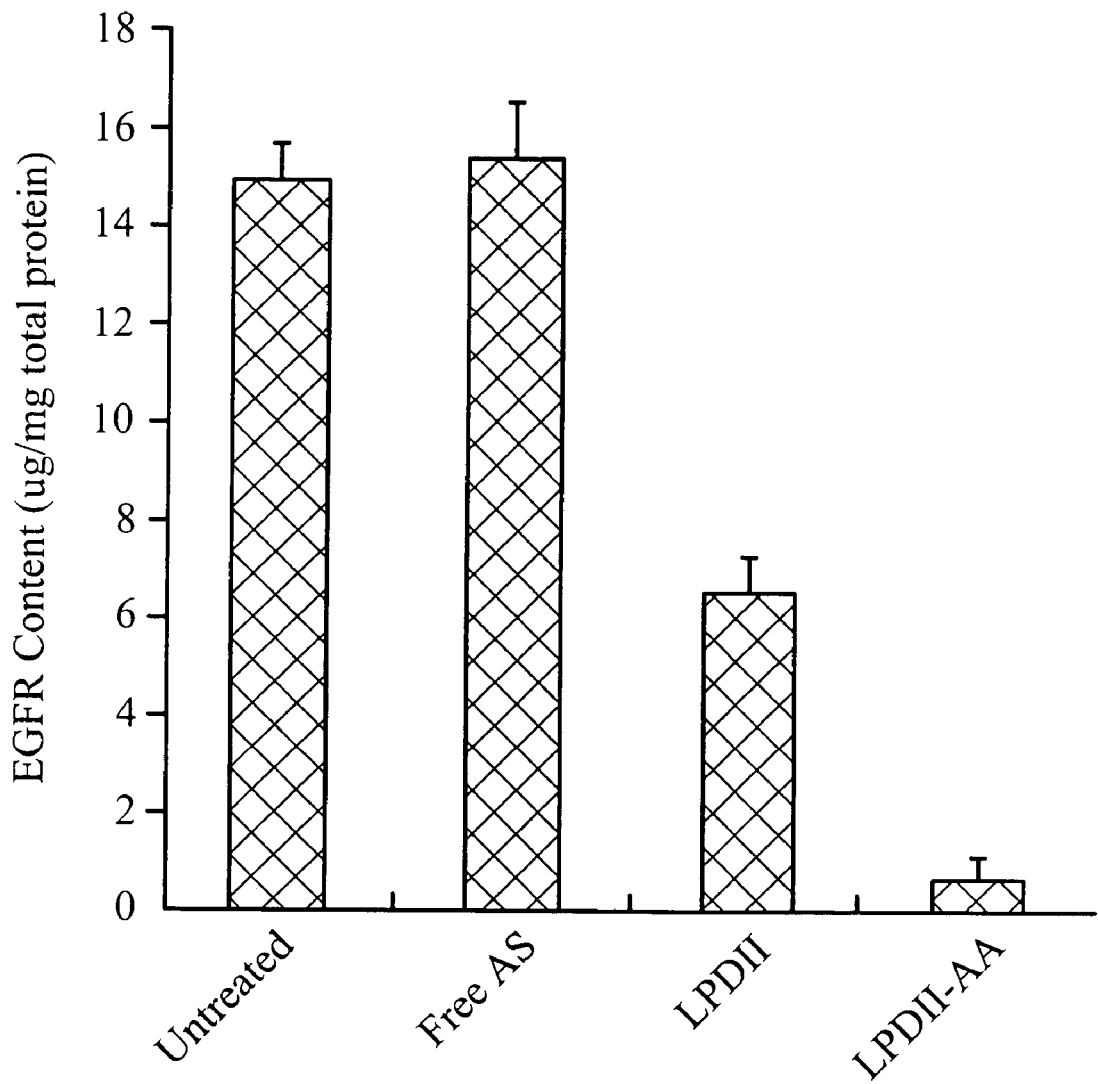

As shown in FIG. 5, in 22B cells, free AS-ODN provides no growth inhibition effect on head and neck cancer cells. Growth inhibition effects of LPDII on 22B or HONE-1 cells was 30% and 65%, respectively. Growth inhibition effects of LPDII-AA reached 90%. In EGFR down-regulation study, as shown in FIG. 6, free AS-ODN had no effect, LPDII down-regulated 50~60% of EGFR expression, and LPDII-AA down-regulated over 95% of EGFR expression.

The results indicate that AA ligand modified LPDII (LPDII-AA) deliver more AS-ODN into sigma receptor over-expressed cells and exert stronger effects.

Example 5

In Vivo Efficacy Test

Figure 7:
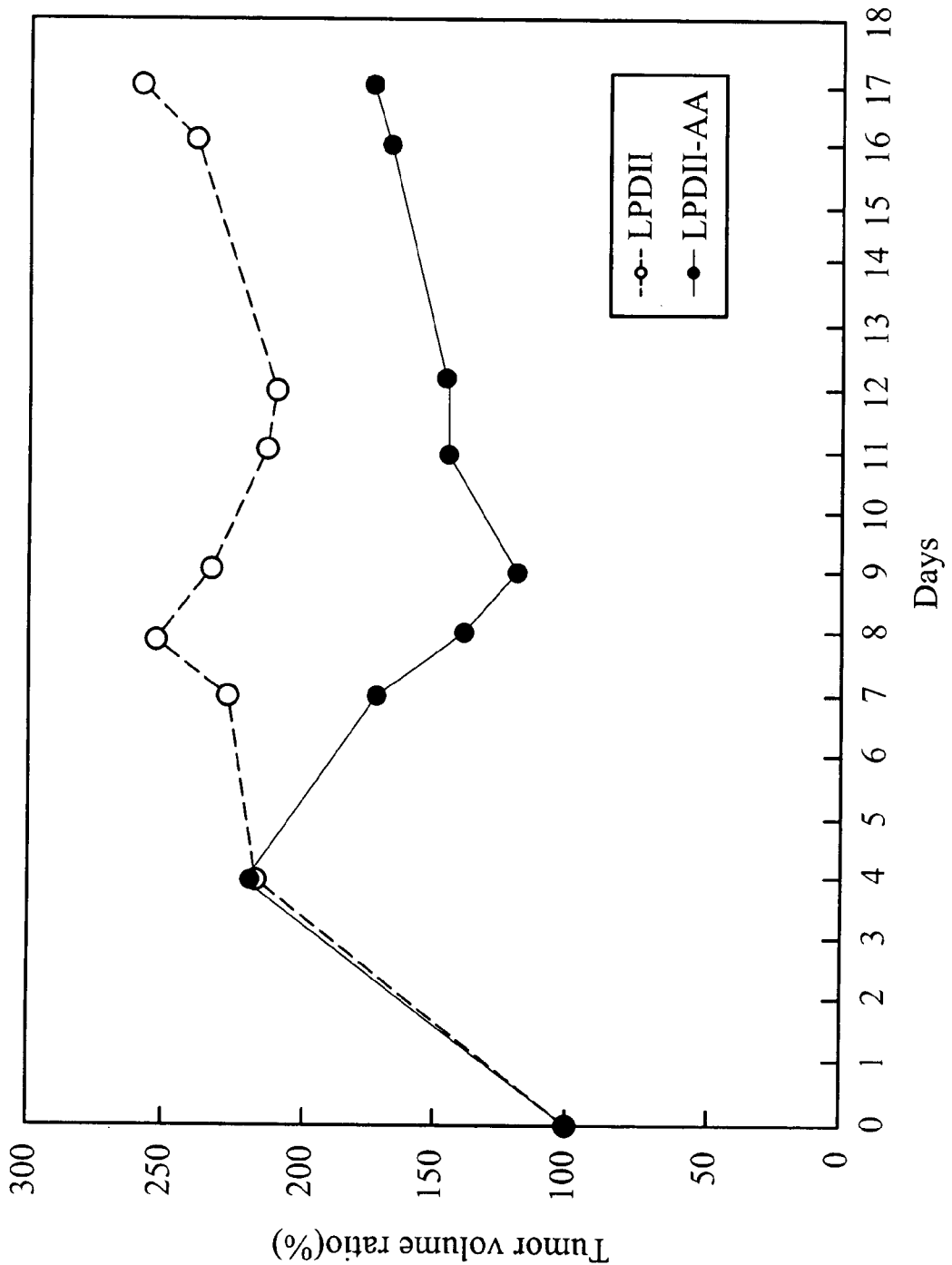
FIG. 7 shows tumor growth inhibition in SCID mice respectively treated with LPDII and LPDII-AA.

1×10$^6$ of 22B cells were subcutaneously injected into the right flank of 6-week-old SCID mice (severe combined immune-deficiency mice) (Harlan Sprague Dawlay, Indianapolis, Ind.). When the tumor was grown to a palpable size, AS-ODN in different formula were injected into the tumor. The tumor size was measured continuously. The results were shown in FIG. 7. The tumor growth inhibition effect of LPDII-AA was 1.5 times higher than that of LPDII.

These results indicate that the targeted delivery system could effectively deliver the anti-tumor drugs into the tumor cells over-expressed SR. For example, the antisense oligonucleotide against EGFR carried by ligand-modified delivery system could effectively inhibit head and neck cancer growth. The delivery efficiency of the targeted delivery system was 2~3 times that of the non-targeted one. The competitive inhibition study also showed the specificity of the targeted delivery system. In addition, the in vitro and in vivo tests showed that antisense oligonucleotide against EGFR delivered by the targeted delivery system significantly inhibited the growth of head and neck cancer.

While the invention has been described by way of example and in terms of preferred embodiment, it is to be understood that the invention is not limited thereto.

What is claimed is:

1. A targeted delivery system, comprising a carrier an encapsulated and a targeted ligand modifying the carrier to target the encapsulated drug to a sigma receptor over-expressed cell, wherein the targeted ligand is and the carrier is liposome.

2. The targeted delivery system as claimed in claim 1, wherein the targeted ligand is conjugated with a lipid to form a ligand conjugated lipid for modification of the carrier.

3. The targeted delivery system as claimed in claim 1, wherein the drug is an organic compound, a peptide, a protein, an oligonucleotide, or DNA.

4. The targeted delivery system as claimed in claim 1, wherein the drug is an oligonucleotide.

5. The targeted delivery system as claimed in claim 1, wherein the drug is an anti-sense oligonucleotide.

6. The targeted delivery system as claimed in claim 1, wherein the sigma receptor over-expressed cell is a tumor cell.

7. The targeted delivery system as claimed in claim 6, wherein the tumor cell is from breast cancer, head and neck cancer, lung cancer, liver cancer, brain, or prostate cancer.

8. The targeted delivery system as claimed in claim 7, wherein the tumor cell is from head and neck cancer.

9. The targeted delivery system as claimed in claim 8, wherein the targeted ligand is conjugated with a lipid to form a ligand-conjugated lipid.

10. The targeted delivery system as claimed in claim 8, wherein the drug is an organic compound, a peptide, a protein, an oligonucleotide, or DNA.

11. The targeted delivery system as claimed in claim 10, wherein the drug is an oligonucleotide.

12. The targeted delivery system as claimed in claim 11, wherein the drug is an anti-sense oligonucleotide.

13. The targeted delivery system as claimed in claim 12, wherein the drug is an anti-sense oligonucleotide against EGFR (epidermal growth factor receptor).

\* \* \* \* \*

UNITED STATES PATENT AND TRADEMARK OFFICE
CERTIFICATE OF CORRECTION

PATENT NO. : 7,803,398 B2  
APPLICATION NO. : 11/020773  
DATED : September 28, 2010  
INVENTOR(S) : Li et al.

Page 1 of 1

It is certified that error appears in the above-identified patent and that said Letters Patent is hereby corrected as shown below:

Col 4, line 60 (claim 1) should read as follows:

Claim 1: A targeted delivery system, comprising a carrier [an] encapsulat<u>ing</u>[ed] <u>a drug</u> and a targeted ligand modifying the carrier to target the encapsulated drug to a sigma receptor over-expressed cell, wherein the targeted ligand is <u>anisamide</u> and the carrier is liposome.

Signed and Sealed this  
Seventeenth Day of May, 2011

David J. Kappos  
*Director of the United States Patent and Trademark Office*